United States Patent
Champagne

(10) Patent No.: US 6,447,292 B1
(45) Date of Patent: Sep. 10, 2002

(54) DENTAL IMPRESSION TRAY AND BITE REGISTRATION RIM ASSEMBLY

(76) Inventor: Richard Champagne, 2334 Orchard Crest Blvd., Manasquan, NJ (US) 08736

( * ) Notice: Subject to any disclaimer, the term of this patent is extended or adjusted under 35 U.S.C. 154(b) by 0 days.

(21) Appl. No.: 09/866,959

(22) Filed: May 29, 2001

(51) Int. Cl.[7] .................................................. A61C 9/00
(52) U.S. Cl. ........................................... 433/45; 433/46
(58) Field of Search ............................... 433/37, 46, 45

(56) References Cited

U.S. PATENT DOCUMENTS

| | | | | |
|---|---|---|---|---|
| 2,428,773 A | * | 10/1947 | Beresin et al. ................. | 433/45 |
| 5,076,785 A | * | 12/1991 | Tsai .............................. | 433/46 |
| 5,551,872 A | * | 9/1996 | Mena ........................... | 433/37 |

* cited by examiner

Primary Examiner—Nicholas D. Lucchesi
(74) Attorney, Agent, or Firm—Kaplan & Gilman, L.L.P.

(57) ABSTRACT

A dental impression tray and bite registration rim assembly comprises an impression tray, a handle and a bite registration rim. The handle and the bite registration rim are both detachably attachable to the impression tray. The connection elements between the handle and the bite registration rim to the impression tray may be the same or different. The handle is attached to the impression tray to facilitate taking of a precise gum impression, but is detached and replaced by the bite registration rim when taking a bite registration. Thus, a precise gum and bite registration may be conveniently taken in a single visit of the patient.

28 Claims, 4 Drawing Sheets

DENTAL IMPRESSION TRAY AND BITE REGISTRATION RIM ASSEMBLY

TECHNICAL FIELD

This invention generally relates to dental devices, and more particularly, to a dental impression tray and bite registration rim assembly which is capable of conveniently taking a precise gum impression and a bite registration in a single visit of a patient.

BACKGROUND OF THE INVENTION

To prepare a set of dentures for a patient, a dentist needs to take an impression for the patient's gum as well as a bite registration for the patient's tooth position and vertical dimension.

Such a procedure usually requires two visits of the patient. In the first visit, the dentist takes a gum impression of the patient by means of an impression tray with an impression material retained therein. For facilitating the maneuver of the impression tray in the patient's mouth so as to take a precise gum impression, a removable handle may be attached to the bottom of the tray. Andreiko in U.S. Pat. No. 5,752,826 discloses an impression tray with an attachable handle. After the gum impression is taken on the impression material, the impression tray is delivered to a laboratory or factory to prepare a gum mold simulating the shape and contour of the gum. Afterwards, a bite registration rim or block, usually made of a wax, is attached to the gum mold. The gum mold, with the bite registration rim attached thereto, is sent back to the dentist. In the second visit, the bite registration rim, together with the gum mold to which it is attached, is inserted into the mouth of the patient, being adjusted inside the mouth, to take a bite registration.

This two-visit procedure is very inconvenient and costly. Zentz et al. in U.S. Pat. No. 6,196,840 B1 discloses custom a fitting variable dimension bite registration dental impression tray which comprises a bite registration member (wax rim) and a dental impression tray. The gum impression and the bite registration may be taken in a single visit of the patient. In Zenta et al, the bite registration member (wax rim) is fixedly secured to the bottom of the impression tray by melting some of the wax into the holes in the bottom of the tray. The impression tray and the wax rim are always together even in the process of only taking the gum impression. This makes it inconvenient to maneuver inside the patent's mouth while taking the gum impression and it is also not comfortable to the patient. Furthermore, there is no handle to facilitate the maneuver of the tray and wax rim inside the patient's mouth. Therefore, it is not easy to use Zentz et al's invention to take a precise gum impression.

SUMMARY OF THE INVENTION

It is an object of the present invention to provide an impression tray and bite registration rim assembly that is capable of conveniently taking a precise gum impression and a bite registration in a single visit of the patient. It is another object of the present invention to provide a method of taking a precise gum impression and bite registration which may be carried out with ease in a single visit of the patient.

According to the invention, a dental impression tray and bite registration rim assembly comprises an impression tray for taking a gum impression, a handle detachably connected to the impression tray by a first connection, and a bite registration rim detachably connected to the impression tray by a second connection. When taking the gum impression, only the handle is attached to the impression tray to facilitate the maneuver of the impression tray inside the mouth of the patient so as to take a precise gum impression. After taking the gum impression, the handle is removed from the impression tray and the bite registration rim is attached to the tray. The impression tray and the bite registration rim, which are now connected together, are inserted into the mouth of the patient to take the bite registration. Only a single visit of the patient is required, and a precise gum impression can be taken conveniently with the help of the handle.

Preferably, the first and the second connections have the same structure such that the bite registration rim and the handle are capable of interchangeably connecting to the impression tray.

BRIEF DESCRIPTION OF THE DRAWINGS

The above and further features and advantages may be clearer after reading the detailed description of preferred embodiments of the present invention with reference to the accompanying drawings, in which.

DETAILED DESCRIPTION OF THE PREFERRED EMBODIMENT

Figure 1:
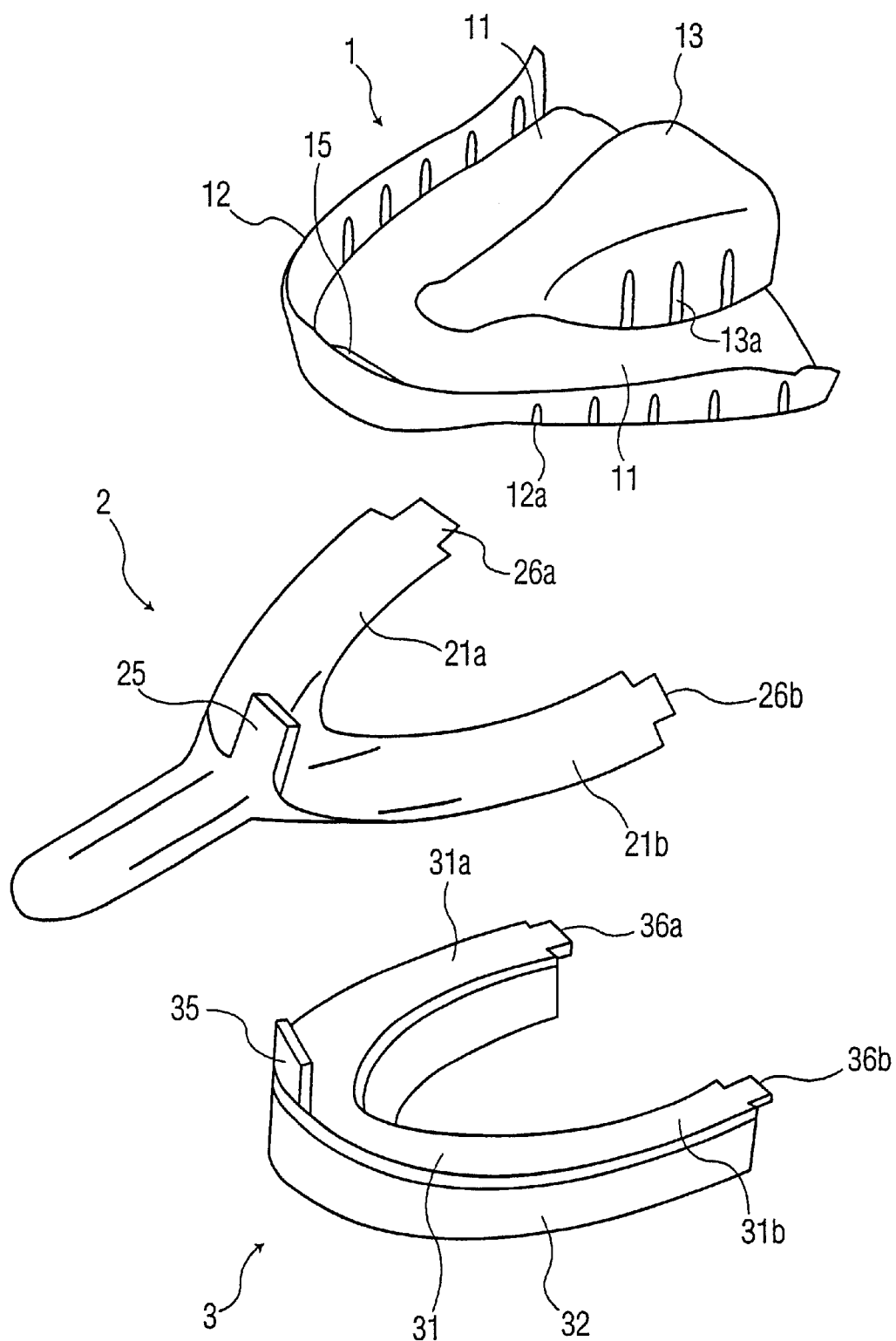
FIG. 1 is a disassembled perspective view of a first embodiment of the dental impression tray and bite registration rim assembly of the present invention.

Reference is made to FIG. 1, in which a first embodiment of the present invention is shown. The dental impression tray and bite registration rim assembly of the present invention comprises three elements, i.e., an impression tray 1, and handle 2 and a bite registration rim 3. The assembly shown in FIG. 1 is for making the upper denture for the patient, but it shall be appreciated that the concept of the invention also applies to the assembly for making the lower denture of the patient. Therefore, only the assembly for the upper denture is described here.

The impression tray 1 is made of a heat adjustable material so that it may be adjusted to match the dimension of a patient's oral structure when it is heated to above its softening point (usually between 38° C. and below 120° C.). The impression tray 1 comprises a U-shaped trough 11, which is formed between a side wall 12 and a central bulge portion 13 which is of a shape and size to correspond to the roof of the mouth of a patient. The U-shaped trough 11 is used to retain a conventional elastomeric impression material (e.g., a silicone elastomer, not shown) which is used to take a gum impression of the patient. Some slots 12a are formed in the side wall 12, and some other slots 13a are formed on a side portion of the central bulge portion 13. These slots 12a and 13a make it easier to deform the impression tray 1 so as to adjust the impression tray 1 following the dimension of the patient's oral structure.

Figure 2:
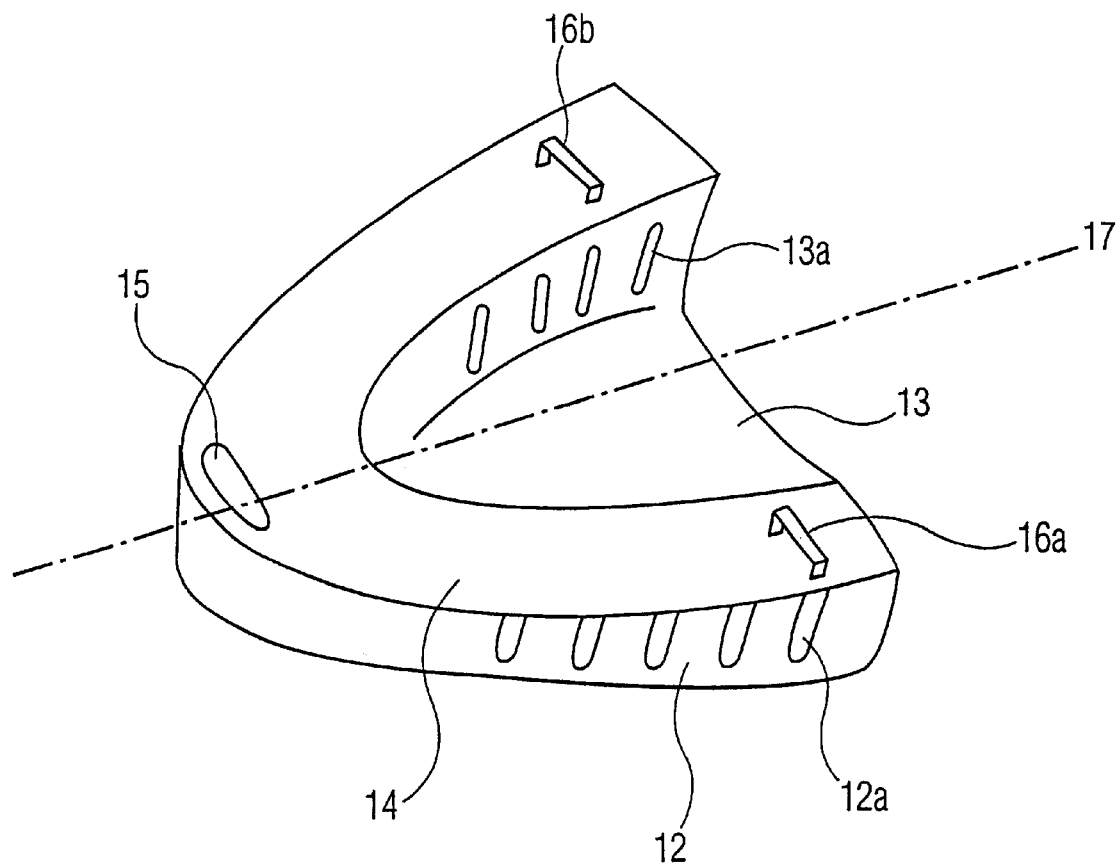
FIG. 2 is a bottom perspective view of the impression tray shown in FIG. 1.
Figure 3:
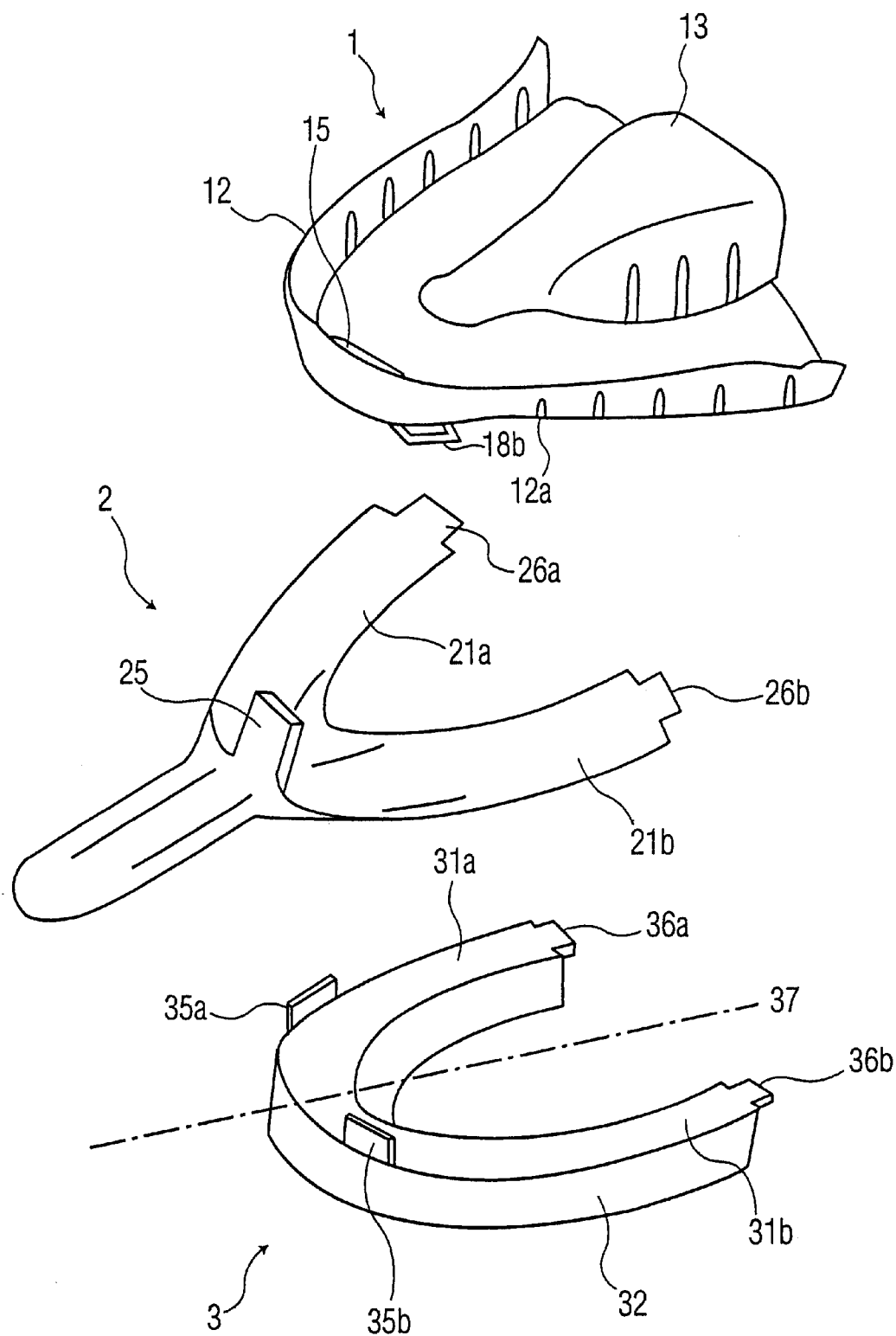
FIG. 3 is a disassembled perspective view of a second embodiment of the dental impression tray and bite registration rim assembly of the present invention.
Figure 4:
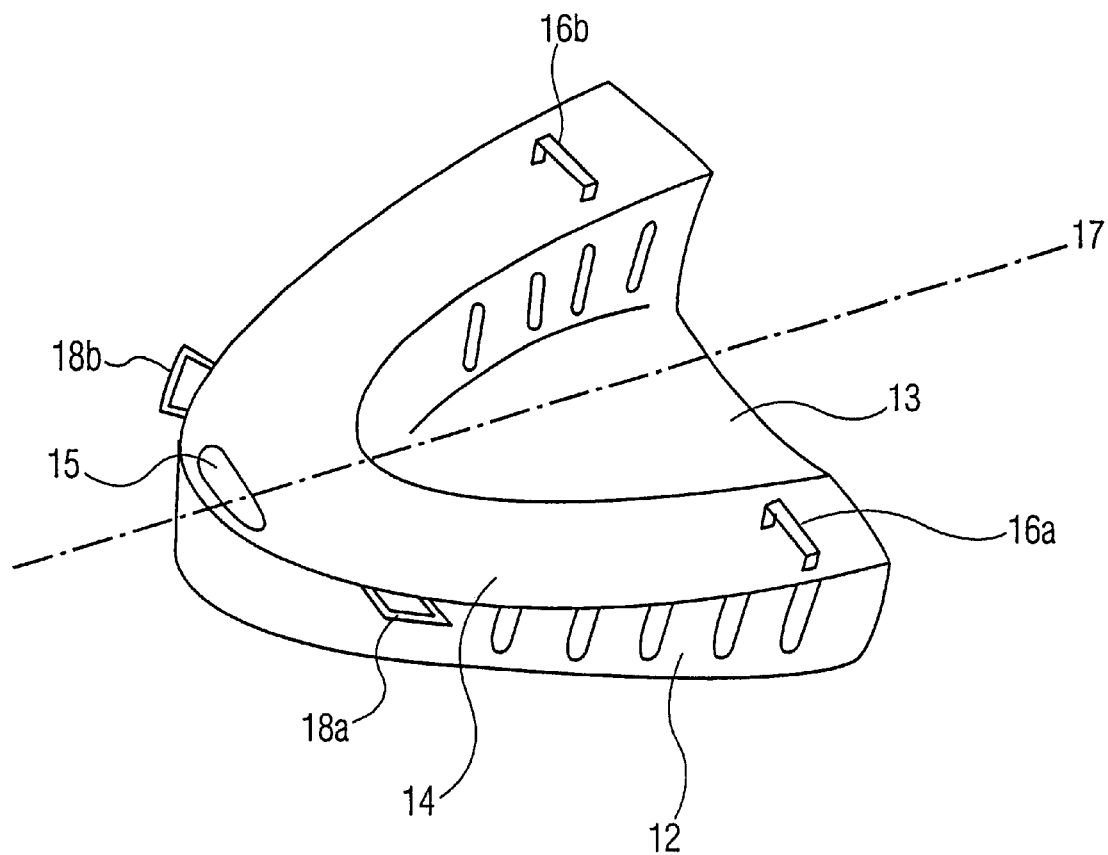
FIG. 4 is a bottom perspective view of the impression tray shown in FIG. 3.

The bottom side of the impression tray 1 is shown in FIG. 2. A U-shaped bottom 14 shown in FIG. 2 is formed opposite to the U-shaped trough 11 shown in FIG. 1. A hole 15 is formed in the bottom 14 at the central juncture of the U-shape. Two slots 16a and 16b are provided on the bottom 14 at the two leg portions of the U-shape, symmetrically to a central axis 17 of the U-shape. The hole 15 and the slots 16a, 16b work to engage with their counterparts of the handle 2 and the bite registration rim 3, which will be explained in more detail later.

The handle 2, which is generally a Y-shaped flat plate, has two leg portions 21 and 22 which generally match the bottom 14 of the impression tray 1. Two tongues 26a and 26b extend from the free ends of the two leg portions 21a and 21b respectively. The two tongues 26a and 26b are capable of being inserted into and engageable with the two slots 16a and 16b respectively. Furthermore, a protrusion 25 is formed on the handle 2 at the juncture of the two leg portions 21a and 21b, extending in a direction perpendicular to a plane of the flat plate of the handle, i.e., formed by the two leg portions 21a and 21b. The protrusion 25 is capable of being inserted into and engageable with the hole 15 in the bottom 14 of the impression tray 1.

The bite registration rim 3 is used for taking a bite registration of the patient and is usually made of a wax. As shown in FIG. 1, the bite registration rim 3 is in U-shape that matches the bottom 14 of the impression tray 1. The bite registration rim 3 in FIG. 1 comprises a base portion 31 and a rim portion 32 secured on the base portion 31, both in U-shape. Preferably the two portions 31 and 32 are made of different materials. Preferably the base portion 31 is made of the same material of the impression tray 1, and the rim portion 32 is made of the wax.

The U-shaped base portion has two leg portions 31a and 31b having tongues 36a and 36b extending from their free ends respectively. A protrusion 35 extends from the base portion 31 at the central juncture of the U-shape in a direction perpendicular to the plane of the base portion 31, i.e., formed by the two leg portions 31a and 31b of the base portion 3. Similar to the tongues 26a, 26b and protrusion 25 on the handle 2, the tongues 36a and 36b are capable of being inserted into and engageable with the slots 16a and 16b respectively, and the protrusion 35 is capable of being inserted into and engageable with the hole 15 in the bottom 14 of the impression tray 1.

In use, the dentist selects a set of the dental impression tray and bite registration rim assembly of a proper size according to the oral dimension of the patient. The handle 2 is connected to the impression tray 1 by inserting the two tongues 16a, 26b into the slots 16a, 16b, and the protrusion 25 into the hole 15, on the bottom 14 of the impression tray 1. The impression tray 1 is then heated to a temperature above its softening point, e.g., in hot water, before it is inserted into the mouth of the patient for adjustment. After the impression tray 1 is adjusted to the oral structure of the patient, an impression material is filled into the trough 11 of the tray 1. With the help of the handle 2, the impression tray 1, now with the impression material filled thereon, is inserted into the patient's mouth to take the gum impression. The handle 2 makes the maneuver of the impression tray 1 inside the patient's mouth very convenient so that a gum impression may be taken precisely.

To take a more precise gum impression, the process of taking gum impression may comprise two steps. First, a roughly preliminary gum impression is taken with the impression tray 1 filled with a medium or heavy body impression material. Then a thin layer of light body impression material (such as Aquasil LV) is applied to the roughly formed preliminary gum impression, and the impression tray 1 is inserted into the patient's mouth immediately to take a precise final gum impression.

After the gum impression is taken, the handle 2 is detached and removed from the tray impression 1. The impression tray 1 is cooled (e.g., in the air) to below the softening point. After being warmed to above its softening point, the bite registration rim 3 is now connected to the impression tray 1 by inserting the tongues 36a, 36b into the slots 16a, 16b, and the protrusion 35 into the hole 15, on the impression tray 1. The impression tray 1 and bite registration rim 3, which are now connected together, are inserted into the mouth of the patient to take the bite registration by adjusting the bite registration rim 3 inside the patient's mouth.

In the embodiment shown in FIG. 1, handle 2 and the bite registration rim 3 have the same connection structure for connecting with the impression tray 1. In particular, both the handle 1 and the bite registration tray 2 use a pair of tongues 26a, 26b and 36a, 36b at the free ends of the two leg portions 21a, 21b and 31a, 31b to engage with the slots 16a, 16b on the bottom 14 of the impression tray 1, and a protrusion 25, 26 at the juncture of the two leg portions 21a, 21b and 31a, 31b to engage with the hole 15 in the bottom 14 of the impression tray 1. Thus, the handle 1 and the bite registration rim 3 are interchangeably attachable to the impression tray 1.

Similarly to FIGS. 1 and 2, FIGS. 3 and 4 show a second embodiment of the invention, in which the same reference numbers are used for designating similar elements in FIGS. 1 and 2. Only the different features are described in detail here.

One of the different features is that the different connection structure between handle 1 and the bite registration rim 3 to the impression tray 1. In particular, another two slots 18a and 18b are provided at the bottom 14 of the impression tray 1 symmetrically (to the central axis 17) extending from the out surface of the sidewall 12 in the plane of the bottom 14. Correspondingly, two protrusions 35a and 35b, symmetric to a central axis 37, extend from the sidewall of the rim portion 32 in a direction perpendicular to a plane formed by the two leg portions 31a and 31b. More protrusions in the rim 3 may provide a more secure connection between the rim 3 and the impression tray 1.

Another feature is that the bite registration rim 3 is a single piece. No base portion is provided in this embodiment. The tongues 36a, 36b and the protrusions 35a, 35b are directly formed on the rim portion 32 which is usually made of a wax.

The preferred embodiments of the invention have been described in detail as above. However, it shall be appreciated that, without departing the spirit of the invention, numerous amendments, changes and modifications are possible to a skilled person in the art. For example, connection elements other than the tongues, protrusion and slots may be used to connect the handle 1 and the bite registration rim 3 to the impression tray. Furthermore, although only the assembly and method for making the upper denture is described in detail in the embodiments, the invention also equally covers an assembly and method for making a lower denture. Therefore, the scope of the invention is solely intended to be set out in the claims.

What is claimed is:

1. A dental impression tray and bite registration rim assembly comprising:
   an impression tray for taking a gum impression;
   a handle, said handle being detachably attachable to said impression tray by a first connection, and
   a bite registration rim, said bite registration rim being detachably attachable to said tray by a second connection.

2. The assembly of claim 1 wherein said first connection and said second connection have a same structure such that said bite registration rim and said handle are capable of interchangeably connecting to said impression tray.

3. The assembly of claim 1 wherein said impression tray is made of a heat adjustable material.

4. The assembly of claim 1 wherein said bite registration rim is made of a wax.

5. The assembly of claim 1 wherein said impression tray has a U-shaped trough portion for accommodating an impression material and a U-shaped flat bottom opposite to said trough portion.

6. The assembly of claim 5 wherein said handle is attachable to said bottom by said first connection.

7. The assembly of claim 5 wherein said bite registration rim is attachable to said bottom by said second connection.

8. The assembly of claim 7 wherein said bite registration rim comprises a rim portion and a flat base portion supporting said rim portion.

9. The assembly of claim 8 wherein said base portion and said rim portion are made from different materials.

10. The assembly of claim 9 wherein said second connection is provided on said flat base portion.

11. The assembly of claim 8 wherein said flat base portion is a U-shaped member having two leg portions.

12. The assembly of claim 11 wherein said second connection comprises:
   two tongues each extending from a free end of each of said two leg portions, and
   two slots provided on said U-shaped bottom of said impression tray, said two slots being engageable to said two tongues respectively.

13. The assembly of claim 11 wherein said second connection further comprises:
   a protrusion extending in a direction perpendicular to a plane formed by said two leg portions of said flat base portion, and
   a hole formed in said U-shaped bottom of said impression tray, said hole being engageable to said protrusion.

14. The assembly of claim 7 wherein said bite registration rim is a U-shaped member
   with two leg portions respectively.

15. The assembly of claim 14 wherein said another two slots are symmetrically provided on an outside wall of said impression tray, and said two protrusions are symmetrically formed along an outer periphery of said bite registration rim.

16. The assembly of claim 14 wherein said second connection comprises:
   two tongues each extending from a free end of each of said two leg portions, and
   two slots provided on said U-shaped bottom of said impression tray, said two slots being engageable with said two tongues respectively.

17. The assembly of claim 16 wherein said connection further comprises:
   two protrusions extending in a direction perpendicular to a plane formed by said two leg portions, and
   another two slots provided on said impression tray, said another two slots being engageable with said two protrusions respectively.

18. The assembly of claim 5 wherein said handle is a Y-shaped flat plate with two leg portions matching said U-shaped bottom of said impression tray.

19. The assembly of claim 18 wherein said connection comprises:
   two tongues each extending from a free end of each of said two leg portions, and
   two slots provided on said U-shaped bottom of said impression tray, said two slots being engageable to said two tongues respectively.

20. The assembly of claim 19 wherein said first connection further comprises:
   a protrusion extending from said handle at a juncture of said two leg portions in a direction perpendicular to a plane of formed by said two leg portions, and
   a hole formed in said U-shaped bottom of said impression tray, said hole being engageable with said protrusion.

21. The assembly of claim 1 wherein said impression tray is an upper tray for taking an impression of upper gum of a patient, and said bite registration rim is an upper rim for taking an upper bite registration.

22. The assembly of claim 1 wherein said impression tray is a lower tray for taking an impression of lower gum of a patient, and said bite registration rim is a lower rim for taking a lower bite registration.

23. A method of taking gum impression and bite registration in a single visit of a patient, said method comprising the steps of:
   a. inserting an impression tray with a handle attached thereon into said patient's mouth;
   b. taking a gum impression of said patient;
   c. removing said handle from said impression tray;
   d. attaching a bite registration rim to said impression tray; and
   e. taking a bite registration of said patient.

24. The method of claim 23 further comprises a step of, before step a), adjusting said impression tray to match said patient's oral structure.

25. The method of claim 24 further comprising a step of, before said adjusting, warming said impression tray to a temperature above its softening point.

26. The method of claim 23 wherein said step b) comprises a step of taking a preliminary gum impression and a step of taking a final gum impression.

27. The method of claim 23 further comprising a step of, after step c), cooling said impression tray to a temperature below its softening point.

28. The method of claim 23 further comprising a step of, before step d), warming said bite registration rim to a temperature above its softening point.

* * * * *